(12) United States Patent
Bojkova

(10) Patent No.: US 9,469,731 B2
(45) Date of Patent: Oct. 18, 2016

(54) EPOXIDE AND THIOEPOXIDE FUNCTIONAL, POLYMERIZABLE COMPOSITION AND METHODS OF PREPARING OPTICAL ARTICLES THEREFROM

(71) Applicant: PPG Industries Ohio, Inc., Cleveland, OH (US)

(72) Inventor: Nina V. Bojkova, Monroeville, PA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 0 days.

(21) Appl. No.: 15/062,889

(22) Filed: Mar. 7, 2016

(65) Prior Publication Data

US 2016/0185910 A1    Jun. 30, 2016

Related U.S. Application Data

(60) Continuation of application No. 13/961,443, filed on Aug. 7, 2013, now Pat. No. 9,279,907, which is a division of application No. 13/706,178, filed on Dec. 5, 2012, now abandoned.

(51) Int. Cl.
| | | |
|---|---|---|
| G02B 1/04 | (2006.01) |
| C08G 75/04 | (2016.01) |
| C07D 331/02 | (2006.01) |
| C08F 220/38 | (2006.01) |

(52) U.S. Cl.
CPC .......... C08G 75/045 (2013.01); C07D 331/02 (2013.01); C08F 220/38 (2013.01); G02B 1/041 (2013.01)

(58) Field of Classification Search
CPC ....................................................... G02B 1/04
USPC .................... 526/273, 256; 528/360; 549/90; 560/152
See application file for complete search history.

(56) References Cited

U.S. PATENT DOCUMENTS 6,117,923 A * 9/2000 Amagai ............... C08G 59/302
                                                            523/440

* cited by examiner

*Primary Examiner* — Ling Choi
*Assistant Examiner* — Chun-Cheng Wang
(74) *Attorney, Agent, or Firm* — The Webb Law Firm

(57) ABSTRACT

Provided is a thioepoxide functional polymerizable composition comprising a reaction product of thiourea and an epoxide functional, polymerizable composition. The epoxide functional, polymerizable composition comprises a reaction product prepared from a reaction mixture comprising:
  (a) a monomer comprising at least one ethylenically unsaturated ester functional monomer having an epoxide functional group; and
  (b) a compound having two or more thiol groups.
The reactants (a) and (b) are reacted via a Michael addition reaction in the presence of a base to form an epoxide functional reaction product. Also provided are methods of preparing an optical article using the polymerizable compositions.

5 Claims, No Drawings

EPOXIDE AND THIOEPOXIDE FUNCTIONAL, POLYMERIZABLE COMPOSITION AND METHODS OF PREPARING OPTICAL ARTICLES THEREFROM

CROSS REFERENCE TO RELATED APPLICATIONS

This application is a continuation of U.S. application Ser. No. 13/961,443, filed Aug. 7, 2013, now U.S. Pat. No. 9,279,907, issued Mar. 8, 2016, which is a divisional of U.S. application Ser. No. 13/706,178, filed on Dec. 5, 2012, now abandoned, which applications are incorporated herein by reference in their entirety.

FIELD OF THE INVENTION

The present invention relates to epoxide functional polymerizable compositions and thioepoxide functional polymerizable compositions that are derived from ethylenically unsaturated monomers having episulfide functional groups in the monomer, and to methods of preparing optical articles from such polymerizable compositions.

BACKGROUND OF THE INVENTION

Polymeric materials, such as plastics, have been developed as alternatives and replacements for silica based inorganic glass in applications such as optical lenses, fiber optics, windows and automotive, nautical and aviation transparencies. These polymeric materials can provide advantages relative to glass, including shatter resistance, lighter weight for a given application, ease of molding and ease of dyeing. Representative examples of such polymeric materials include poly(methyl methacrylate), polycarbonate and poly(diethylene glycol bis(allylcarbonate)).

The refractive indices of many polymeric materials are generally lower than that of high index glass. For example, the refractive index of poly(diethylene glycol bis(allylcarbonate)) is about 1.50, compared to that of high index glass, which can range, for example, from 1.60 to 1.80.

Polymeric materials (polymerizates) prepared from the polymerization of monomers containing aromatic rings and/or sulfur typically have high refractive indices. Polymeric materials having a combination of high refractive indices, such as at least 1.57, and low levels of chromatic dispersion (e.g., having ABBE numbers of at least 30), can be prepared from monomers containing certain heteroatoms, such as sulfur atoms. Such polymerizates are very useful in the making of optical elements requiring superior optical properties.

It would be desirable to develop polymerizable compositions that provide desirable optical properties to an optical article prepared therefrom, such as high refractive index and high ABBE number, with low cost and simple processing.

SUMMARY OF THE INVENTION

In accordance with the present invention, there is provided a thioepoxide functional, polymerizable composition comprising a reaction product of thiourea and an epoxide functional polymerizable composition. The epoxide functional polymerizable composition comprises a reaction product of:

(a) a monomer comprising at least one ethylenically unsaturated ester functional monomer having an epoxide functional group; and
(b) a compound having two or more thiol groups.

The reactants (a) and (b) are reacted via a Michael addition reaction in the presence of a base to form an epoxide functional reaction product.

Also provided are methods of preparing an optical article. In a first embodiment, the method comprises:

(1) reacting together:
  (a) a monomer comprising at least one ethylenically unsaturated ester functional monomer having an epoxide functional group; and
  (b) a compound having two or more thiol groups, wherein the reactants (a) and (b) are reacted via a Michael addition reaction in the presence of a base to form an epoxide functional reaction product;
(2) reacting the epoxide functional reaction product formed in step (1) with thiourea to form a thioepoxide functional, polymerizable composition;
(3) mixing the thioepoxide functional, polymerizable composition formed in step (2) with:
  (a) a polymerizable composition comprising at least one ethylenically unsaturated (meth)acrylate functional monomer having a thioepoxide functional group;
  (b) an addition polymerization initiator; and
  (c) a catalyst to form a reaction mixture;
(4) introducing the reaction mixture formed in step (3) to a mold of a desired shape at a temperature and for a time sufficient to form a polymerizate; and
(5) releasing the polymerizate from the mold to yield an optical article.

In a separate embodiment, the method comprises:

(1) reacting together the following reactants:
  (a) a monomer comprising at least one ethylenically unsaturated ester functional monomer having an epoxide functional group; and
  (b) a compound having two or more thiol groups, wherein the reactant (a) is present in stoichiometric excess and the reactants (a) and (b) are reacted via a Michael addition reaction in the presence of a base to form a product mixture comprising an epoxide functional reaction product and excess monomer (a);
(2) reacting the product mixture formed in step (1) with thiourea to form a thioepoxide functional, polymerizable composition;
(3) preparing a prepolymer reactant mixture by:
  (i) mixing the thioepoxide functional, polymerizable composition formed in step (2) with:
    (a) a first polymerizable composition comprising at least one ethylenically unsaturated monomer; and
    (b) an azo addition polymerization initiator to form a reaction mixture; and
  (ii) allowing ethylenically unsaturated groups in the reaction mixture formed in (i) to polymerize to form a prepolymer having a threshold viscosity of 50 to 500 centipoise measured at 25° C. wherein the azo addition polymerization initiator is present in an amount sufficient only to achieve the threshold viscosity;
(4) mixing the prepolymer reactant mixture formed in step (3) with:
  (a) an initiator package that is essentially free of azo initiators; and
  (b) a second polymerizable composition comprising at least one ethylenically unsaturated monomer having two or more ethylenically unsaturated groups to form a moldable composition;

(5) introducing the moldable composition formed in step (4) to a mold of a desired shape at a temperature and for a time sufficient to form a polymerizate; and (6) releasing the polymerizate from the mold to yield an optical article.

DETAILED DESCRIPTION OF THE INVENTION

As used herein, molecular weight values of polymers, such as weight average molecular weights (Mw) and number average molecular weights (Mn), are determined by gel permeation chromatography using appropriate standards, such as polystyrene standards.

As used herein, polydispersity index (PDI) values represent a ratio of the weight average molecular weight (Mw) to the number average molecular weight (Mn) of the polymer (i.e., Mw/Mn).

As used herein, the term "polymer" means homopolymers (e.g., prepared from a single monomer species), and copolymers (e.g., prepared from at least two monomer species).

As used herein, the term "(meth)acrylate" and similar terms, such as (meth)acryloyl and (meth)acrylic acid ester, means methacrylate and acrylate. Either or both, when they exist, may be present in a composition.

As used herein, the term "thio(meth)acrylate" and similar terms, such as thio(meth)acryloyl and thio(meth)acrylic acid ester, means thiomethacrylate and thioacrylate, as above.

As used herein, recitations of "linear or branched" groups, such as linear or branched alkyl, are understood to include a methylene group or a methyl group; groups that are linear, such as linear $C_2$-$C_{25}$ alkyl groups; and groups that are appropriately branched, such as branched $C_3$-$C_{25}$ alkyl groups.

As used herein, the term "halo" and similar terms, such as halo group, halogen, halogen group, halide, and halide group means F, Cl, Br and/or I, such as fluoro, chloro, bromo and/or iodo.

Unless otherwise indicated, all ranges or ratios disclosed herein are to be understood to encompass any and all subranges or subratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as, but not limited to, 1 to 6.1, 3.5 to 7.8, and 5.5 to 10.

As used herein, the articles "a", "an", and "the" include plural referents unless otherwise expressly and unequivocally limited to one referent.

Other than in the operating examples, or where otherwise indicated, all numbers expressing quantities of ingredients, reaction conditions, and so forth used in the specification and claims are to be understood as modified in all instances by the term "about".

The epoxide functional polymerizable compositions of the present invention comprise a reaction product prepared from a reaction mixture comprising (a) a monomer comprising at least one ethylenically unsaturated, ester functional monomer having an epoxide functional group; and (b) a compound having two or more thiol groups (polythiol). Examples of suitable monomers (a) include, for example, glycidyl (meth)acrylate, glycidyl maleates and/or fumarates, and the like. The presence of the ester functional group in the epoxide functional monomer allows for Michael addition of the thiol to the ethylenic double bond to take place between the epoxide functional monomer and the polythiol, provided the carbon-oxygen double bond in the ester group is conjugated with the ethylenic unsaturation in the monomer.

Suitable polythiols are thiol-containing materials that may have at least two thiol functional groups and may comprise a dithiol, or a mixture of a dithiol and a compound having more than two thiol functional groups (higher polythiol). Such mixtures may include mixtures of dithiols, mixtures of higher polythiols and/or mixtures of dithiols with higher polythiols. The thiol functional groups are typically terminal groups, though a minor portion (i. e., less than 50 percent of all groups) may be pendant along a chain. The compound (b) may additionally contain a minor portion of other active hydrogen functionality (i.e., different from thiol), for example, hydroxyl functionality. Thiol-containing materials may be linear or branched, and may contain cyclic, alkyl, aryl, aralkyl, or alkaryl groups.

Suitable dithiols can include linear or branched aliphatic, cycloaliphatic, aromatic, heterocyclic, polymeric, oligomeric dithiols and mixtures thereof. The dithiol can comprise a variety of linkages including, but not limited to, ether linkages (—O—), sulfide linkages (—S—), polysulfide linkages (-Sx-, wherein x is at least 2, or from 2 to 4), ester linkages, urethane linkages, and combinations of such linkages.

Non-limiting examples of suitable dithiols for use in the present invention can include, but are not limited to, 2,5-dimercaptomethyl-1,4-dithiane, bis(2-mercaptoethyl)sulfide (dimercaptodiethylsulfide or "DMDS"), ethanedithiol, 3,6-dioxa-1,8-octanedithiol, ethylene glycol di(2-mercaptoacetate), ethylene glycol di(3-mercaptopropionate), poly(ethylene glycol) di(2-mercaptoacetate) and poly(ethylene glycol) di(3-mercaptopropionate), benzenedithiol, 4-tert-butyl-1,2-benzenedithiol, 4,4'-thiodibenzenethiol, pentaerythritol tetrakis(2-mercaptoacetate), pentaerythritol tetrakis(3-mercaptopropionate), trimethylolpropane tris(2-mercaptoacetate), trimethylolpropane tris(3-mercaptopropionate), and mixtures thereof.

The dithiol may include dithiol oligomers having disulfide linkages, such as materials represented by the following formula:

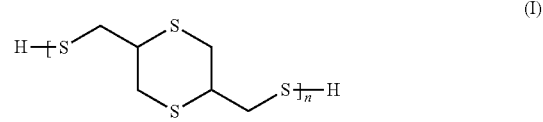

(I)

wherein n can represent an integer from 1 to 21.

Dithiol oligomers represented by Formula I can be prepared, for example, by the reaction of 2,5-dimercaptomethyl-1,4-dithiane with sulfur in the presence of basic catalyst, as known in the art.

The nature of the SH group in polythiols is such that oxidative coupling can occur readily, leading to formation of disulfide linkages. Various oxidizing agents can lead to such oxidative coupling. The oxygen in the air can, in some cases, lead to such oxidative coupling during storage of the polythiol. It is believed that a possible mechanism for the oxidative coupling of thiol groups involves the formation of thiyl radicals, followed by coupling of said thiyl radicals, to form disulfide linkage. It is further believed that formation of disulfide linkage can occur under conditions that can lead to the formation of thiyl radical, including but not limited to reaction conditions involving free radical initiation. The polythiols can include species containing disulfide linkages formed during storage.

The polythiols for use as compound (b) in the preparation of the polymerizable composition of the present invention can also include species containing disulfide linkages formed during synthesis of the polythiol.

In certain embodiments, the dithiol for use in the present invention can include at least one dithiol represented by the following structural formulas:

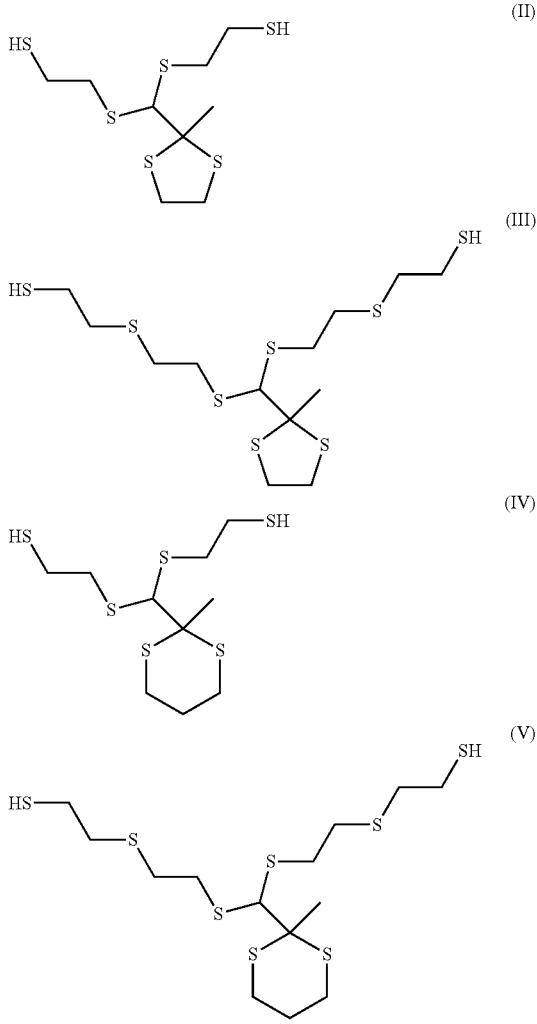

The sulfide-containing dithiols comprising 1,3-dithiolane (e.g., formulas II and III) or 1,3-dithiane (e.g., formulas IV and V) can be prepared by reacting asym-dichloroacetone with dimercaptan, and then reacting the reaction product with dimercaptoalkylsulfide, dimercaptan or mixtures thereof, as described in U.S. Pat. No. 7,009,032 B2.

Non-limiting examples of suitable dimercaptans for use in the reaction with asym-dichloroacetone can include but are not limited to materials represented by the following formula:

wherein Y can represent $CH_2$ or $(CH_2-S-CH_2)$, and n can be an integer from 0 to 5. The dimercaptan for reaction with asym-dichloroacetone in the present invention can be chosen from, for example, ethanedithiol, propanedithiol, and mixtures thereof.

The amount of asym-dichloroacetone and dimercaptan suitable for carrying out the above reaction can vary. For example, asym-dichloroacetone and dimercaptan can be present in the reaction mixture in an amount such that the molar ratio of dichloroacetone to dimercaptan can be from 1:1 to 1:10.

Suitable temperatures for reacting asym-dichloroacetone with dimercaptan can vary, often ranging from 0 to 100° C.

Non-limiting examples of suitable dimercaptans for use in the reaction with the reaction product of the asym-dichloroacetone and dimercaptan, can include but are not limited to materials represented by the above general formula VI, aromatic dimercaptans, cycloalkyl dimercaptans, heterocyclic dimercaptans, branched dimercaptans, and mixtures thereof.

Non-limiting examples of suitable dimercaptoalkylsulfides for use in the reaction with the reaction product of the asym-dichloroacetone and dimercaptan can include materials represented by the following formula:

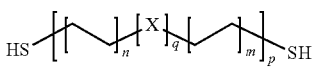

wherein X can represent O, S or Se, n can be an integer from 0 to 10, m can be an integer from 0 to 10, p can be an integer from 1 to 10, q can be an integer from 0 to 3, and with the proviso that (m+n) is an integer from 1 to 20.

Non-limiting examples of suitable dimercaptoalkylsulfides for use in the present invention can include branched dimercaptoalkylsulfides.

The amount of dimercaptan, dimercaptoalkylsulfide, or mixtures thereof, suitable for reacting with the reaction product of asym-dichloroacetone and dimercaptan, can vary. Typically, dimercaptan, dimercaptoalkylsulfide, or a mixture thereof, can be present in the reaction mixture in an amount such that the equivalent ratio of reaction product to dimercaptan, dimercaptoalkylsulfide, or a mixture thereof, can be from 1:1.01 to 1:2. Moreover, suitable temperatures for carrying out this reaction can vary within the range of from 0 to 100° C.

The reaction of asym-dichloroacetone with dimercaptan can be carried out in the presence of an acid catalyst. The acid catalyst can be selected from a wide variety known in the art, such as but not limited to Lewis acids and Bronsted acids. Non-limiting examples of suitable acid catalysts can include those described in Ullmann's Encyclopedia of Industrial Chemistry, 5th Edition, 1992, Volume A21, pp. 673 to 674. The acid catalyst is often chosen from boron trifluoride etherate, hydrogen chloride, toluenesulfonic acid, and mixtures thereof. The amount of acid catalyst can vary from 0.01 to 10 percent by weight of the reaction mixture.

The reaction product of asym-dichloroacetone and dimercaptan can alternatively be reacted with dimercaptoalkylsulfide, dimercaptan or mixtures thereof, in the presence of a base. The base can be selected from a wide variety known in the art, such as but not limited to Lewis bases and Bronsted bases. Non-limiting examples of suitable bases can include those described in Ullmann's Encyclopedia of Industrial Chemistry, 5th Edition, 1992, Volume A21, pp. 673 to 674. The base is often sodium hydroxide. The amount of base can vary. Typically, a suitable equivalent ratio of base to reaction product of the first reaction can be from 1:1 to 10:1.

The reaction of asym-dichloroacetone with dimercaptan can be carried out in the presence of a solvent. The solvent can be selected from but is not limited to organic solvents. Non-limiting examples of suitable solvents can include but are not limited to chloroform, dichloromethane, 1,2-dichloroethane, diethyl ether, benzene, toluene, acetic acid and mixtures thereof.

In another embodiment, the reaction product of asym-dichloroacetone and dimercaptan can be reacted with dimercaptoalkylsulfide, dimercaptan or mixtures thereof, with or without the presence of a solvent, wherein the solvent can be selected from but is not limited to organic solvents. Non-limiting examples of suitable organic solvents can include alcohols such as but not limited to methanol, ethanol and propanol; aromatic hydrocarbon solvents such as but not limited to benzene, toluene, xylene; ketones such as but not limited to methyl ethyl ketone; water; and mixtures thereof.

The reaction of asym-dichloroacetone with dimercaptan can also be carried out in the presence of a dehydrating reagent. The dehydrating reagent can be selected from a wide variety known in the art. Suitable dehydrating reagents for use in this reaction can include but are not limited to magnesium sulfate. The amount of dehydrating reagent can vary widely according to the stoichiometry of the dehydrating reaction.

The polythiols for use as compound (b) can be prepared in certain non-limiting embodiments by reacting 2-methyl-2-dichloromethyl-1,3-dithiolane with dimercaptodiethylsulfide to produce dimercapto-1,3-dithiolane derivative of formula III. Alternatively, 2-methyl-2-dichloromethyl-1,3-dithiolane can be reacted with 1,2-ethanedithiol to produce dimercapto-1,3-dithiolane derivative of formula II. 2-methyl-2-dichloromethyl-1,3-dithiane can be reacted with dimercaptodiethylsulfide to produce dimercapto-1,3-dithiane derivative of formula V. Also, 2-methyl-2-dichloromethyl-1,3-dithiane can be reacted with 1,2-ethanedithiol to produce dimercapto-1,3-dithiane derivative of formula IV.

Another non-limiting example of a dithiol suitable for use as the material (ii) can include at least one dithiol oligomer prepared by reacting dichloro derivative with dimercaptoalkylsulfide as follows:

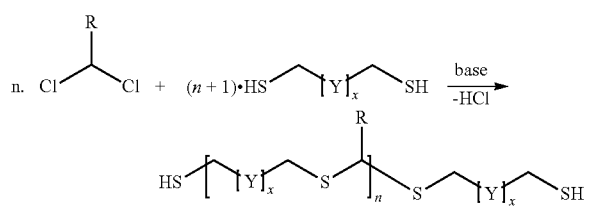

wherein R can represent $CH_3$, $CH_3CO$, $C_1$ to $C_{10}$ alkyl, cycloalkyl, aryl alkyl, or alkyl-CO; Y can represent $C_1$ to $C_{10}$ alkyl, cycloalkyl, $C_6$ to $C_{14}$ aryl, $(CH_2)_p(S)_m(CH_2)_q$, $(CH_2)_p(Se)_m(CH_2)_q$, $(CH_2)_p(Te)_m(CH_2)_q$, wherein m can be an integer from 1 to 5 and, p and q can each be an integer from 1 to 10; n can be an integer from 1 to 20; and x can be an integer from 0 to 10.

The reaction of dichloro derivative with dimercaptoalkylsulfide can be carried out in the presence of a base. Suitable bases include any known to those skilled in the art in addition to those disclosed above.

The reaction of dichloro derivative with dimercaptoalkylsulfide may be carried out in the presence of a phase transfer catalyst. Suitable phase transfer catalysts for use in the present invention are known and varied. Non-limiting examples can include but are not limited to tetraalkylammonium salts and tetraalkylphosphonium salts. This reaction is often carried out in the presence of tetrabutylphosphonium bromide as phase transfer catalyst. The amount of phase transfer catalyst can vary widely, from 0 to 50 equivalent percent, or from 0 to 10 equivalent percent, or from 0 to 5 equivalent percent, relative to the dimercaptosulfide reactants.

The polythiols for use as compound (b) may further contain hydroxyl functionality. Non-limiting examples of suitable materials having both hydroxyl and multiple (more than one) thiol groups can include but are not limited to glycerin bis(2-mercaptoacetate), glycerin bis(3-mercaptopropionate), 1,3-dimercapto-2-propanol, 2,3-dimercapto-1-propanol, trimethylolpropane bis(2-mercaptoacetate), trimethylolpropane bis(3-mercaptopropionate), pentaerythritol bis(2-mercaptoacetate), pentaerythritol tris(2-mercaptoacetate), pentaerythritol bis(3-mercaptopropionate), pentaerythritol tris(3-mercaptopropionate), and mixtures thereof.

In addition to dithiols disclosed above, particular examples of suitable dithiols can include 1,2-ethanedithiol, 1,2-propanedithiol, 1,3-propanedithiol, 1,3-butanedithiol, 1,4-butanedithiol, 2,3-butanedithiol, 1,3-pentanedithiol, 1,5-pentanedithiol, 1,6-hexanedithiol, 1,3-dimercapto-3-methylbutane, dipentenedimercaptan, ethylcyclohexyldithiol (ECHDT), dimercaptodiethylsulfide (DMDS), methyl-substituted dimercaptodiethylsulfide, dimethyl-substituted dimercaptodiethylsulfide, 3,6-dioxa-1,8-octanedithiol, 1,5-dimercapto-3-oxapentane, 2,5-dimercaptomethyl-1,4-dithiane (DMMD), ethylene glycol di(2-mercaptoacetate), ethylene glycol di(3-mercaptopropionate), and mixtures thereof.

Suitable trifunctional or higher-functional polythiols for use as compound (b) can be selected from a wide variety known in the art. Non-limiting examples can include pentaerythritol tetrakis(2-mercaptoacetate), pentaerythritol tetrakis(3-mercaptopropionate), trimethylolpropane tris(2-mercaptoacetate), trimethylolpropane tris(3-mercaptopropionate), 2,3(bis((2-mercaptoethyl)thio)-1-propanethiol (GST), and/or thioglycerol bis(2-mercaptoacetate).

For example, the polythiol can be chosen from materials represented by the following general formula,

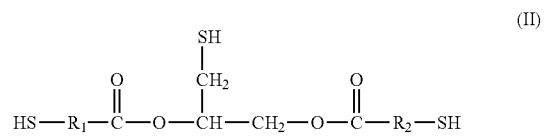

(II)

wherein $R_1$ and $R_2$ can each be independently chosen from straight or branched chain alkylene, cyclic alkylene, phenylene and $C_1$-$C_9$ alkyl substituted phenylene. Non-limiting examples of straight or branched chain alkylene can include methylene, ethylene, 1,3-propylene, 1,2-propylene, 1,4-butylene, 1,2-butylene, pentylene, hexylene, heptylene, octylene, nonylene, decylene, undecylene, octadecylene and icosylene. Non-limiting examples of cyclic alkylenes can include cyclopentylene, cyclohexylene, cycloheptylene, cyclooctylene, and alkyl-substituted derivatives thereof. The divalent linking groups $R_1$ and $R_2$ can be chosen from methylene, ethylene, phenylene, and alkyl-substituted phenylene, such as methyl, ethyl, propyl, isopropyl and nonyl substituted phenylene.

In particular embodiments, a polythiol may be prepared by reacting together (1) any of the dithiols mentioned above, and (2) a compound having at least two double bonds (for example, a diene) or a compound containing a triple bond.

The compound (2) having triple bond functionality may comprise any known alkyne, for example, propargyl alcohol, propargyl chloride, propargyl bromide, propargyl acetate, propargyl propionate, propargyl benzoate, phenyl acetylene, phenyl propargyl sulfide, 1,4-dichloro-2-butyne, 2-butyne-1,4-diol, 3-butyne-2-ol, 2-pentyne, 1-hexyne, 2-hexyne, 3-hexyne, 3-hexyne-2,5-diol, and/or mixtures thereof.

The compound (2) having at least two double bonds can be chosen from non-cyclic dienes, including straight chain and/or branched aliphatic non-cyclic dienes, non-aromatic ring-containing dienes, including non-aromatic ring-containing dienes wherein the double bonds can be contained within the ring or not contained within the ring or any combination thereof, and wherein the non-aromatic ring-containing dienes can contain non-aromatic monocyclic groups or non-aromatic polycyclic groups or combinations thereof; aromatic ring-containing dienes; or heterocyclic ring-containing dienes; or dienes containing any combination of such non-cyclic and/or cyclic groups. The dienes can optionally contain thioether, disulfide, polysulfide, sulfone, ester, thioester, carbonate, thiocarbonate, urethane, or thiourethane linkages, or halogen substituents, or combinations thereof; with the proviso that the dienes contain double bonds capable of undergoing reaction with SH groups of a polythiol, and forming covalent C—S bonds. Often the compound (2) having at least two double bonds comprises a mixture of dienes that are different from one another.

The compound (2) having at least two double bonds may comprise acyclic non-conjugated dienes, acyclic polyvinyl ethers, allyl-(meth)acrylates vinyl-(meth)acrylates, di(meth)acrylate esters of diols, di(meth)acrylate esters of dithiols, di(meth)acrylate esters of poly(alkyleneglycol) diols, monocyclic non-aromatic dienes, polycyclic non-aromatic dienes, aromatic ring-containing dienes, diallyl esters of aromatic ring dicarboxylic acids, divinyl esters of aromatic ring dicarboxylic acids, and/or mixtures thereof.

Non-limiting examples of acyclic non-conjugated dienes can include those represented by the following general formula:

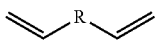

wherein R can represent $C_1$ to $C_{30}$ linear or branched divalent saturated alkylene radical, or $C_2$ to $C_{30}$ divalent organic radical including groups such as but not limited to those containing ether, thioether, ester, thioester, ketone, polysulfide, sulfone and combinations thereof. The acyclic non-conjugated dienes can be selected from 1,5-hexadiene, 1,6-heptadiene, 1,7-octadiene and mixtures thereof.

Non-limiting examples of suitable acyclic polyvinyl ethers can include those represented by the following structural formula:

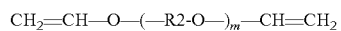

wherein $R_2$ can be $C_2$ to $C_6$ n-alkylene, $C_3$ to $C_6$ branched alkylene group, or $-[(CH_2-)_p-O-]_q-(-CH_2-)_r-$, m can be a rational number from 0 to 10, often 2; p can be an integer from 2 to 6, q can be an integer from 1 to 5 and r can be an integer from 2 to 10.

Non-limiting examples of suitable polyvinyl ether monomers for use can include divinyl ether monomers, such as ethylene glycol divinyl ether, diethylene glycol divinyl ether, triethyleneglycol divinyl ether, and mixtures thereof.

Di(meth)acrylate esters of linear diols can include ethanediol di(meth)acrylate, 1,3-propanediol dimethacrylate, 1,2-propanediol di(meth)acrylate, 1,4-butanediol di(meth)acrylate, 1,3-butanediol di(meth)acrylate, 1,2-butanediol di(meth)acrylate, and mixtures thereof.

Di(meth)acrylate esters of dithiols can include, for example, di(meth)acrylate of 1,2-ethanedithiol including oligomers thereof, di(meth)acrylate of dimercaptodiethyl sulfide (i.e., 2,2'-thioethanedithiol di(meth)acrylate) including oligomers thereof, di(meth)acrylate of 3,6-dioxa-1,8-octanedithiol including oligomers thereof, di(meth)acrylate of 2-mercaptoethyl ether including oligomers thereof, di(meth)acrylate of 4,4'-thiodibenzenethiol, and mixtures thereof.

Further non-limiting examples of suitable dienes can include monocyclic aliphatic dienes such as those represented by the following structural formula:

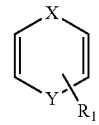

wherein X and Y each independently can represent $C_1$-$C_{10}$ divalent saturated alkylene radical; or $C_1$-$C_5$ divalent saturated alkylene radical, containing at least one element selected from the group of sulfur, oxygen and silicon in addition to the carbon and hydrogen atoms; and $R_1$ can represent H, or $C_1$-$C_{10}$ alkyl; and

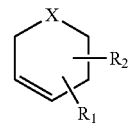

wherein X and $R_1$ can be as defined above and $R_2$ can represent $C_2$-$C_{10}$ alkenyl. The monocyclic aliphatic dienes can include 1,4-cyclohexadiene, 4-vinyl-1-cyclohexene, dipentene and terpinene.

Non-limiting examples of polycyclic aliphatic dienes can include 5-vinyl-2-norbornene; 2,5-norbornadiene; dicyclopentadiene and mixtures thereof.

Non-limiting examples of aromatic ring-containing dienes can include those represented by the following structural formula:

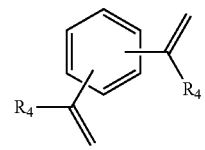

wherein $R_4$ can represent hydrogen or methyl. Aromatic ring-containing dienes can include monomers such as diisopropenyl benzene, divinyl benzene and mixtures thereof.

Examples of diallyl esters of aromatic ring dicarboxylic acids can include but are not limited to those represented by the following structural formula:

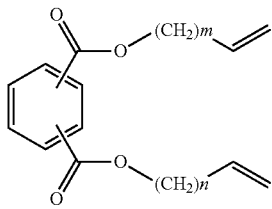

wherein m and n each independently can be an integer from 0 to 5. The diallyl esters of aromatic ring dicarboxylic acids can include o-diallyl phthalate, m-diallyl phthalate, p-diallyl phthalate and mixtures thereof.

Often, the compound (2) having at least two double bonds comprises 5-vinyl-2-norbornene, ethylene glycol divinyl ether, diethylene glycol divinyl ether, triethylene glycol divinyl ether, butane diol divinyl ether, vinylcyclohexene, 4-vinyl-1-cyclohexene, dipentene, terpinene, dicyclopentadiene, cyclododecadiene, cyclooctadiene, 2-cyclopenten-1-yl-ether, 2,5-norbornadiene, divinylbenzene including 1,3-divinylbenzene, 1,2-divinylbenzene, and 1,4-divinylbenzene, diisopropenylbenzene including 1,3-diisopropenylbenzene, 1,2-diisopropenylbenzene, and 1,4-diisopropenylbenzene, allyl (meth)acrylate, ethanediol di(meth)acrylate, 1,3-propanediol di(meth)acrylate, 1,2-propanediol di(meth)acrylate, 1,3-butanediol di(meth)acrylate, 1,2-butanediol di(meth)acrylate, ethylene glycol di(meth) acrylate, diethylene glycol di(meth)acrylate, dimercaptodiethylsulfide di(meth)acrylate, 1,2-ethanedithiol di(meth) acrylate, and/or mixtures thereof.

Other non-limiting examples of suitable di(meth)acrylate monomers can include ethylene glycol di(meth)acrylate, 1,3-butylene glycol di(meth)acrylate, 1,4-butanediol di(meth)acrylate, 2,3-dimethyl-1,3-propanediol di(meth)acrylate, 1,6-hexanediol di(meth)acrylate, propylene glycol di(meth) acrylate, dipropylene glycol di(meth)acrylate, tripropylene glycol di(meth)acrylate, tetrapropylene glycol di(meth)acrylate, ethoxylated hexanediol di(meth)acrylate, propoxylated hexanediol di(meth)acrylate, neopentyl glycol di(meth)acrylate, alkoxylated neopentyl glycol di(meth)acrylate, hexylene glycol di(meth)acrylate, diethylene glycol di(meth) acrylate, polyethylene glycol di(meth)acrylate, thiodiethyleneglycol di(meth)acrylate, trimethylene glycol di(meth)acrylate, triethylene glycol di(meth)acrylate, alkoxylated hexanediol di(meth)acrylate, alkoxylated neopentyl glycol di(meth)acrylate, pentanediol di(meth)acrylate, cyclohexane dimethanol di(meth)acrylate, and ethoxylated bis-phenol A di(meth)acrylate.

As noted above, the reactants (a) and (b) are reacted together via a Michael addition reaction. Typically the reactants are combined with the monomer (a) in stoichiometric excess. For example, the molar ratio of the polythiol compound (b) to the monomer (a) is usually 1:2.

The reactants are reacted in the presence of a base to form the epoxide functional reaction product. Suitable bases include Lewis bases such as 1,4-diazabicyclo[2.2.2]octane (DABCO); tertiary amines, phosphines, and the like.

In accordance with the present invention, a thioepoxide functional polymerizable composition may be prepared by reacting the epoxide functional reaction product described above with thiourea. In the exemplary reaction scheme below, an epoxide functional Michael addition reaction product of glycidyl methacrylate and bis(2-mercaptoethyl) sulfide is reacted with thiourea:

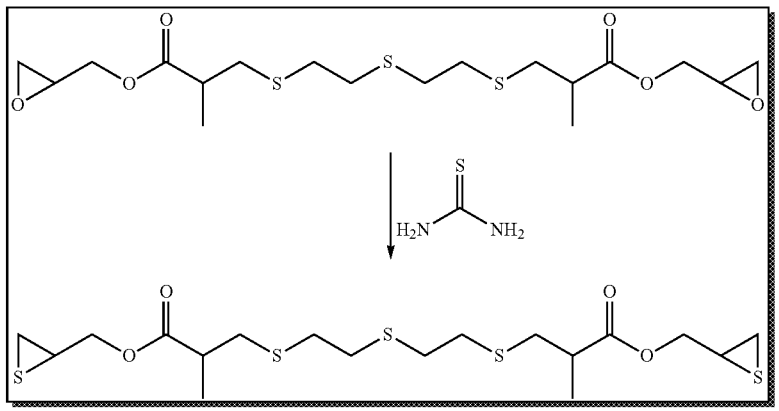

Due to the high reactivity of thioepoxide groups in the presence of bases, it is advisable to add the thiourea to the epoxide functional reaction product after the Michael addition reaction of the epoxide functional monomer having ethylenically unsaturated groups and the polythiol, in order to avoid formation of unwanted polymeric by-products and to ensure formation of the thioepoxide functional polymerizable composition.

In a further embodiment of the present invention, an additional polymerizable composition may be prepared, comprising a reaction product of (a) a monomer composition comprising at least one ethylenically unsaturated (meth) acrylate functional monomer having a thioepoxide functional group and (b) the thioepoxide functional polymerizable composition described above. Examples of such monomers (a) include thioglycidyl methacrylate.

In such a polymerizable composition, the monomer composition (a) may further comprise at least one different polymerizable ethylenically unsaturated monomer. Ethylenically unsaturated groups include (meth)acryloyl, allyl, and/or vinyl groups. Useful alkyl esters of acrylic acid or methacrylic acid include aliphatic alkyl esters containing from 1 to 30, and preferably 4 to 18 carbon atoms in the alkyl group, which may be linear, branched, cyclic, and/or substituted. Representative alkyl groups include but are not limited to methyl, ethyl, propyl, isopropyl, butyl, isobutyl, sec-butyl, tert-butyl, pentyl, neopentyl, hexyl, heptyl, octyl, nonyl, decyl, and structural isomers thereof. Representative cycloalkyl groups include but are not limited to cyclopropyl, cyclobutyl, cyclopentyl, cyclohexyl, and cyclooctyl substituents. Representative poly-fused-ring cycloalkyl groups include but are not limited to decahydronaphthalenyl, tetradecahydroanthracenyl, and tetradecahydrophenanthrenyl. Representative polycyclicalkyl groups include but are not limited to bicyclo[2.2.1]heptanyl (norbornyl), and bicyclo [2.2.2]octanyl. Representative heterocycloalkyl groups include but are not limited to tetrahydrofuranyl, tetrahydropyranyl and piperidinyl, including but not limited to piperidin-4-yl. Representative polycyclicheterocycloalkyl groups include but are not limited to 7-thiabicyclo[2.2.1]heptanyl, 7-oxabicyclo[2.2.1]heptanyl, and 7-azabicyclo[2.2.1]heptanyl. Representative aralkyl groups include but are not limited to benzyl and phenethyl. Examples of monomers having a single ethylenically unsaturated radically polymerizable group that can be present in the monomer composition (a) of the polymerizable compositions of the present invention include, but are not limited to: acrylic acid; methacrylic acid; esters of acrylic acid such as methyl or ethyl acrylate and 2-hydroxyethyl acrylate; esters of methacrylic acid, such as methyl or ethyl methacrylate, phenoxyethyl methacrylate, isobornyl methacrylate, cyclohexyl methacrylate and 2-hydroxyethyl methacrylate; allyl esters, e.g., allyl benzoate; allyl carbonates, e.g., phenyl allyl carbonate; vinyl esters such as vinyl acetate; styrene; and vinyl chloride. In some embodiments, the monoethylenically unsaturated monomers include methyl methacrylate, isobornyl methacrylate, phenoxyethyl methacrylate, cyclohexyl methacrylate, styrene and mixtures thereof. Monomers having more than one ethylenically unsaturated group, such as divinyl benzene (DVB), may also be used in the monomer composition (a). The ethylenically unsaturated monomer(s), when used, is typically present in an amount of from 1 percent by weight to 60 percent by weight, based on the total monomer weight of the polymerizable composition, such as from 3 percent by weight to 55 percent by weight, or from 20 to 45 percent by weight, based on the total monomer weight of the polymerizable composition.

In this embodiment, the monomer composition (a) is typically present in the polymerizable composition of the present invention in an amount of 25 to 90 percent by weight, such as 25 to 75 percent by weight, or 50 to 60 percent by weight based on the total weight of resin solids in the polymerizable composition, while the thioepoxide functional, polymerizable composition (b) is typically present in an amount of 10 to 75 percent by weight, such as 25 to 75 percent by weight, or 40 to 50 percent by weight based on the total weight of resin solids in the polymerizable composition.

The polymerizable compositions described above may be used to prepare optical articles demonstrating high refractive indices. In one embodiment of the present invention, a method of preparing an optical article comprises:

(1) reacting together:
  (a) a monomer comprising at least one ethylenically unsaturated ester functional monomer having an epoxide functional group; and
  (b) a compound having two or more thiol groups, wherein the reactants (a) and (b) are reacted via a Michael addition reaction in the presence of a base to form an epoxide functional reaction product;
(2) reacting the epoxide functional reaction product formed in step (1) with thiourea to form a thioepoxide functional, polymerizable composition;
(3) mixing the thioepoxide functional, polymerizable composition formed in step (2) with:
  (a) a polymerizable composition comprising at least one ethylenically unsaturated (meth)acrylate functional monomer having a thioepoxide functional group;
  (b) an addition polymerization initiator; and
  (c) a catalyst to form a reaction mixture;
(4) introducing the reaction mixture formed in step (3) to a mold of a desired shape at a temperature and for a time sufficient to form a polymerizate; and
(5) releasing the polymerizate from the mold to yield an optical article.

Steps (1) and (2) are described in detail above. In step (3), a reaction mixture is prepared by mixing the thioepoxide functional, polymerizable composition formed in step (2) with a polymerizable composition comprising at least one ethylenically unsaturated (meth)acrylate functional monomer having a thioepoxide functional group, an addition polymerization initiator, and a catalyst to form a reaction mixture.

Suitable addition polymerization initiators include peroxy type initiators known in the art. Azo type initiators should be avoided immediately prior to molding of the polymerizable composition in order to avoid appearance problems caused by gas evolution during reaction.

The polymerizable composition used in step (3) may comprise a prepolymer having a viscosity of 50 to 500 centipoise measured at 25° C. The viscosity may be controlled by careful addition of polymerization initiator. In the making of the prepolymer, any conventional polymerization initiator may be used including azo initiators; in fact, azo initiators are recommended for the prepolymerization. However, care should be taken to remove azo initiators from the prepolymer prior to molding for reasons noted above. The prepolymer may be prepared by polymerizing an ethylenically unsaturated (meth)acrylate functional monomer having a thioepoxide functional group. Optionally, at least one different polymerizable ethylenically unsaturated monomer, including any of those disclosed above such as styrene, may be polymerized with the thioepoxide functional monomer.

The catalyst used in step (3) effects or promotes reaction between the beta-epithiopropyl (thioepoxide) functional groups. The catalyst is present in an amount at least sufficient to effect reaction among the beta-epithiopropyl functional groups in the polymerizable composition, such that the beta-epithiopropyl functional groups react with each other in a chemical reaction such as a polymerization reaction.

Suitable catalysts may include one or more of: phosphines; quaternary phosphonium salts; 1,4-diazabicyclo [2.2.2]octane, also known as 1,4-diazabicyclo[2.2.2]octane or triethylenediamine; other amine catalysts such as amines having a heterocyclic ring; quaternary ammonium salts; tertiary sulfonium salts; secondary iodonium salts; boron trihalides and complexes thereof; organic acids and esters thereof; and metal halides.

Examples of amines having a heterocyclic ring include imidazoles such as imidazole, N-methylimidazole, N-methyl-2-mercaptoimidazole, 2-methylimidazole, 4-methylimidazole, N-ethylimidazole, 2-ethylimidazole, 4-ethylimidazole, N-butylimidazole, 2-butylimidazole, N-undecylimidazole, 2-undecylimidazole, N-phenylimidazole, 2-phenylimidazole, N-benzylimidazole, 2-benzylimidazole, 1-benzyl-2-methylimidazole, N-(2'-cyanoethyl)-2-methylimidazole, N-(2'-cyanoethyl)-2-undecylimidazole, N-(2'-cyanoethyl)-2-phenylimidazole, 3,3-bis(2-ethyl-4-methylimidazolyl)methane, adducts of alkylimidazole and isocyanuric acid, condensates of alkylimidazole and formaldehyde, and the like; and amidines such as 1,8-diazabicyclo[5.4.0]undecene, 1,5-diazabicyclo[4.3.0]nonene, 5,6-dibutylamino-1, 8-diazabicyclo[5.4.0]undecene, and the like.

Specific examples of suitable phosphines include trimethylphosphine, triethylphosphine, triisopropylphosphine, tributylphosphine, tricyclohexylphosphine, trioctylphosphine, triphenylphosphine, tribenzylphosphine, tris(2-methylphenyl)phosphine, tris(3-methylphenyl)phosphine, tris(4-methylphenyl)phosphine, tris(diethylamino)phosphine, dimethylphenylphosphine, diethylphenylphosphine, dicyclohexylphenylphosphine, diethylphenylphosphine, dicyclohexylphenylphosphine, ethyldiphenylphosphine, diphenylcyclohexylphosphine, chlorodiphenylphosphine, and the like.

Examples of quaternary ammonium salts that may be used as a catalyst include tetramethylammoniumchloride, tetramethylammoniumbromide, tetramethylammoniumacetate, tetraethylammoniumchloride, tetraethylammoniumbromide, tetraethylammoniumacetate, tetra-n-butylammoniumfluoride, tetra-n-butylammoniumchloride, tetra-n-butylammoniumbromide, tetra-n-butylammoniumiodide, tetra-n-butylammoniumacetate, tetra-n-butylammoniumborohydride, tetra-n-butylammoniumhexafluorophosphite, tetra-n-butylammoniumhydrogensulphite, tetra-n-butylammoniumtetrafluoroborate, tetra-n-butylammoniumtetraphenylborate, tetra-n-butylammoniumparatoluenesulfonate, tetra-n-hexylammoniumchloride, tetra-n-hexylammoniumbromide, tetra-n-hexylammoniumacetate, tetra-n-octylammoniumchloride, tetra-n-octylammoniumbromide, tetra-n-octylammoniumacetate, trimethyl-n-octylammoniumchloride, trimethylbenzylammoniumchloride, trimethylbenzylammoniumbromide, triethyl-n-octylammoniumchloride, triethylbenzylammoniumchloride, triethylbenzylammoniumbromide, tri-n-butyl-n-octylammoniumchloride, tri-n-butylbenzylammoniumfluoride, tri-n-butylbenzylammoniumchloride, tri-n-butylbenzylammoniumbromide, tri-n-butylbenzylammoniumiodide, methyltriphenylammoniumchloride, methyltriphenylammoniumbromide, ethyltriphenylammoniumchloride, ethyltriphenylammoniumbromide, n-butyltriphenylammoniumchloride, n-butyltriphenylammoniumbromide, 1-methylpyridiniumbromide, 1-ethylpyridiniumbromide, 1-n-butylpyridiniumbromide, 1-n-hexylpyridiniumbromide, 1-n-octylpyridiniumbromide, 1-n-dodecylpyridiniumbromide, 1-phenylpyridiniumbromide, 1-methylpicoliniumbromide, 1-ethylpicoliniumbromide, 1-n-butylpicoliniumbromide, 1-n-hexylpicoliniumbromide, 1-n-octylpicoliniumbromide, 1-n-dodecylpicoliniumbromide, 1-phenylpicoliniumbromide, and the like.

Specific examples of suitable quaternary phosphonium salts include tetramethylphosphoniumchloride, tetramethylphosphoniumbromide, tetraethylphosphoniumchloride, tetraethylphosphoniumbromide, tetra-n-butylphosphoniumchloride, tetra-n-butylphosphoniumbromide, tetra-n-butylphosphoniumiodide, tetra-n-hexylphosphoniumbromide, tetra-n-octylphosphoniumbromide, methyltriphenylphosphoniumbromide, methyltriphenylphosphoniumiodide, ethyltriphenylphosphoniumbromide, ethyltriphenylphosphoniumiodide, n-butyltriphenylphosphoniumbromide, n-butyltriphenylphosphoniumiodide, n-hexyltriphenylphosphoniumbromide, n-octyltriphenylphosphoniumbromide, tetraphenylphosphoniumbromide, tetrakishydroxymethylphosphoniumchloride, tetrakishydroxymethylphosphoniumbromide, tetrakishydroxyethylphosphoniumchloride, tetrakishydroxybutylphosphoniumchloride, and the like.

Specific examples of the tertiary sulfonium salts include trimethylsulfoniumbromide, triethylsulfoniumbromide, tri-n-butylsulfoniumchloride, tri-n-butylsulfoniumbromide, tri-n-butylsulfoniumiodide, tri-n-butylsulfoniumtetrafluoroborate, tri-n-hexylsulfoniumbromide, tri-n-octylsulfoniumbromide, triphenylsulfoniumchloride, triphenylsulfoniumbromide, triphenylsulfoniumiodide, and the like.

Suitable secondary iodonium salts include diphenyliodoniumchloride, diphenyliodoniumbromide, diphenyliodoniumiodide, and the like.

Specific examples of the boron trihalides and complexes thereof include boron trifluoride, boron trifluoride-ethylether complex, boron trifluoride-n-butylether complex, boron trifluoride-phenol complex, boron trifluoride-ethylamine complex, boron trifluoride-piperidine complex, boron trifluoride-acetic acid complex, boron trifluoride-triethanolamine complex, boron trifluoride-ammonia complex, and the like.

Examples of catalytic organic acids and esters thereof include sulfonic acid, carboxylic acid, and esters thereof. Specific examples thereof include methanesulfonic acid, trifluoromethanesulfonic acid, benzenesulfonic acid, p-toluenesulfonic acid, 10-chamfer sulfonic acid, and methyl and ethylesters thereof.

Specific examples of metal halides include zinc chloride, iron chloride, aluminum chloride, tin chloride, titanium chloride, methylaluminum dichloride, ethylaluminum dichloride, dimethylaluminum chloride, and diethylaluminum chloride.

The amount of catalyst present in the reaction mixture is sufficient to effect reaction between the beta-epithiopropyl functional groups in the reaction mixture. The amount of the catalyst is typically 0.001 to 3% by weight, such as 0.005 to 2% by weight, based on the total weight of resin solids in the reaction mixture.

In certain embodiments of the present invention, additional reactants may be added to the reaction mixture immediately prior to introducing the reaction mixture to the mold. For example, at least one different polymerizable ethylenically unsaturated monomer, including any of those disclosed above, may be added to the reaction mixture. In addition or alternatively, at least one compound having two or more beta-epithiopropyl functional groups but no polymerizable ethylenically unsaturated groups may be added to the reaction mixture. Examples of such compounds include bis(beta-epithiopropyl)sulfide, bis(beta-epithiopropyl)disulfide, and bis(beta-epithiopropyloxyphenyl)propane. Bis(beta-epithiopropyloxyphenyl)propane, also called Bisphenol A dithioglycidylether, may be formed as a reaction product of a reaction composition comprising 2,2-bis(4-glycidyloxyphenyl)propane and thiourea. The 2,2-bis(4-glycidyloxyphenyl)propane may be formed as a reaction product of a reaction composition comprising 2,2-bis(4-hydroxyphenyl)propane (Bisphenol A) and epichlorohydrin.

The thermal cure cycle used to cure the polymerizable compositions of the present invention, with some embodiments, involves heating the polymerizable composition in the presence of the initiator from room temperature up to 50° C. to 150° C., over a period of from 2 hours to 48 hours, or from 55° C. up to 90° C. or 100° C. over a period of from 12 to 24 hours, or from 65° C. up to 115° C. or 125° C. over a period of from 12 to 24 hours.

Polymerization of the reaction mixtures of the present invention results in the formation of a polymerizate, which can be in the form of a shaped article. Polymerizates obtained from polymerization of the polymerizable compositions of the present invention are solid, and with some embodiments, transparent. Transparent polymerizates prepared from the polymerizable compositions of the present invention, can be used in optical or ophthalmic applications.

Polymerizates prepared from the polymerizable compositions of the present invention can be used to form solid articles such as optical element(s) or device(s). As used herein, the term "optical" means pertaining to or associated with light and/or vision. For example, the optical element or device can comprise ophthalmic elements and devices, display elements and devices, windows, mirrors, and/or active and passive liquid crystal cell elements and devices. As used herein, the term "ophthalmic" means pertaining to or associated with the eye and vision. Non-limiting examples of ophthalmic elements include corrective and non-corrective lenses, including single vision or multi-vision lenses, which may be either segmented or non-segmented multi-vision lenses (such as, but not limited to, bifocal lenses, trifocal lenses and progressive lenses), as well as other elements used to correct, protect, or enhance (cosmetically or otherwise) vision, including, without limitation, contact lenses, intra-ocular lenses, magnifying lenses, and protective lenses or visors. As used herein, the term "display" means the visible or machine-readable representation of information in words, numbers, symbols, designs or drawings. Non-limiting examples of display elements and devices include screens, monitors, and security elements, such as security marks. As used herein, the term "window" means an aperture adapted to permit the transmission of radiation therethrough. Non-limiting examples of windows include automotive and aircraft transparencies, filters, shutters, and optical switches. As used herein, the term "mirror" means a surface that specularly reflects a large fraction of incident light.

In step (4) of the method of the present invention, the reaction mixture may be introduced into a mold of any desired shape at a temperature and for a time to form a polymerizate. The second reaction mixture typically undergoes an exothermic reaction, and after mixing it is introduced, usually by injection, into a mold. The temperature of the reaction mixture as it is introduced into the mold is usually up to 130° C., often up to 120° C. The reaction mixture is held in the mold at a temperature and for a time sufficient to essentially cure the reaction mixture and form a molded optical article. The mold may have any shape desired for the final product as noted above. It is typically a lens mold; often a mold for an ophthalmic lens. The molded article may then be released from the mold. Optical articles prepared by the process of the present invention demonstrate high yield, high transparency, very low haze, low flow lines and low inclusions. Moreover, the optical articles prepared by the method of the present invention demonstrate a refractive index of at least 1.57.

In an embodiment of the present invention wherein the optical article is a lens, the reaction mixture, which can be optionally degassed, can be introduced into a mold and the mold can be heated (i.e., using a thermal cure cycle) using a variety of conventional techniques known in the art. The thermal cure cycle can vary depending on the reactivity and molar ratio of the reactants, and the presence of catalyst(s). In particular embodiments for lenses, the thermal cure cycle can include heating the mixture from room temperature to a temperature of 200° C. over a period of from 0.5 hours to 120 hours; or from 80 to 150° C. for a period of from 5 hours to 72 hours.

In a particular embodiment of the present invention, the method comprises the following steps:

(1) reacting together:
  (a) a monomer comprising at least one ethylenically unsaturated ester functional monomer having an epoxide functional group; and
  (b) a compound having two or more thiol groups, wherein the reactant (a) is present in stoichiometric excess and the reactants (a) and (b) are reacted via a Michael addition reaction in the presence of a base to form a product mixture comprising an epoxide functional reaction product and excess monomer (a);

(2) reacting the product mixture formed in step (1) with thiourea to form a thioepoxide functional, polymerizable composition;

(3) preparing a prepolymer reactant mixture by:
  (i) mixing the thioepoxide functional, polymerizable composition formed in step (2) with:
    (a) a first polymerizable composition comprising at least one ethylenically unsaturated monomer; and
    (b) an azo addition polymerization initiator to form a reaction mixture; and
  (ii) allowing ethylenically unsaturated groups in the reaction mixture formed in (i) to polymerize to form a prepolymer having a threshold viscosity of 50 to 500 centipoise measured at 25° C., wherein the azo addition polymerization initiator is present in an amount sufficient only to achieve the threshold viscosity;

(4) mixing the prepolymer reactant mixture formed in step (3) with:
  (a) an initiator package that is essentially free of azo initiators; and
  (b) a second polymerizable composition comprising at least one ethylenically unsaturated monomer having two or more ethylenically unsaturated groups to form a moldable composition;

(5) introducing the moldable composition formed in step (4) to a mold of a desired shape at a temperature and for a time sufficient to form a polymerizate; and (6) releasing the polymerizate from the mold to yield an optical article.

In this embodiment of the present invention, in step (1), the equivalent ratio of ethylenically unsaturated groups in the monomer (a) to thiol groups in the compound (b) is often greater than 1.1:1, and can be any ratio up to 99:1, such as 2:1, 5:1, 10:1, etc.

In step (4) of this embodiment, the initiator package (a) typically comprises peroxy functional initiators and a catalyst for ring-opening polymerization. The ethylenically unsaturated monomer having two or more ethylenically unsaturated groups may be any of those disclosed above; it is most often divinylbenzene.

Optical articles prepared using the polymerizable compositions of the present invention typically demonstrate high refractive indices, such as at least 1.57, and high ABBE numbers, such as at least 35.

The present invention is more particularly described in the following examples, which are intended to be illustrative only, since numerous modifications and variations therein

19 will be apparent to those skilled in the art. Unless otherwise specified, all parts and percentages are by weight.

EXAMPLES

The analytical procedures used to determine the properties of the prepared materials and the abbreviations used herein are described in Part 1. Part 2 describes the preparation of Comparative Example 1 (thioglycidyl methacrylate). Part 3 describes the preparation of Examples 1 to 11. Part 4 describes the procedure used for preparing casting a polymer sample of Examples 1, 2, 8-11 and CE-1 and the properties of the polymerizates.

Part 1

Analytical Procedures

All $^1$H NMR data was obtained using a Bruker spectrometer operating at a nominal proton frequency of 500.13 MHz. All spectra were obtained using CDCl$_3$ as the solvent. All IR data were obtained using a Bruker FRA-106/s FT-Raman system utilizing representative peaks at 1655-1616 cm$^{-1}$ to identify the C=C bonds of styrene and the methacrylate, and peaks at 675-640 cm$^{-1}$ to identify the C—S—C bonds of the thioepoxide.

The refractive index ((RI-(E-Line)) of polymer samples was measured using a Metricon Model 2010M prism coupler according to ASTM C1648-06. The refractive index of liquid samples was measured using an Atago DR-M2 Abbe Refractometer at 546 nm (mercury e-line) and 20° C. in accordance with ASTM-D1218-02 (2007).

The viscosity of the liquid samples was measured using Brookfield CAP 2000+ viscometer using spindle #1 at 1000 RPM at 25° C. The viscosity is reported in centipoise (cP). The microindentation hardness or Fischer microhardness (FMH), measured according to ISO 14577-07 using a Fischerscope H-100SMC available from Fischer Technology, Inc. The Fischer microhardness of the polymerizates, ±3 N/mm$^2$, was measured at a load of 300 mN, following a load application of 0-300 mN in 15 s.

The Yellowness Index (YI) was measured using a HunterLab UltraSan PRO according to ASTM E313-10. The path length for sheet samples was equal to the sample thickness (3 mm) and the path length for liquid samples was 2 cm.

The Glass Transition Temperature (Tg) was determined by Dynamic Mechanical Analysis according to ASTM E1640-09 and is reported in ° C.

In addition to the abbreviations provided above, in the examples below, the following abbreviations have the following meanings. If an abbreviation is not defined, it has its generally accepted meaning.

BPA-TDGE=bisphenol A dithioglycidyl ether
DABCO=diazabicyclooctane
DMDS=dimercaptodiethylsulfide
DVB=divinyl benzene
GMA=glycidyl methacrylate
GST=2,3-bis((2-mercaptoethyl)thio)-1-propanethiol
MMA=methyl methacrylate
PTMA=pentaerythritol tetrakis(2-mercaptoacetate)
TBPB=tetra butyl phosphonium bromide
TGMA=thioglycidyl methacrylate Part 2

Preparation of Comparative Example 1 (CE-1) (TGMA)

A 5-L jacketed reactor was fitted with a mechanical stirrer, a thermometer, and a condenser. The vessel was charged

20 with GMA (508 g, 3.58 mol), acetic anhydride (40.2 g, 0.39 mol), methanol (700 mL), and toluene (700 mL) under a nitrogen atmosphere. The mixture was heated to 40° C., and thiourea (300 g, 3.95 mol) was added in 50 g portions in 15 minute intervals. During these additions, the temperature of the reaction was monitored to maintain a temperature range of 40° C.-50° C. After the final portion was added, the reaction was stirred at this temperature for an additional hour after which TLC analysis (30% ethylacetate in hexanes) showed no remaining GMA. The reaction mixture was poured into a 4-L separatory funnel and washed twice with 700 mL portions of dilute H$_2$SO$_4$ (1 weight percent in water) and then washed twice with 700 mL portions of aqueous saturated sodium chloride solution. The organic layer was separated, recovered and stabilized with MEHQ (4-methoxyphenol) (44 mg, 0.36 mmol), dried over magnesium sulfate, and concentrated under vacuum. Clear oil was obtained upon concentration (480 g). The purity of the resulting product was determined by NMR (97.5% TGMA with 2.5% GMA). $^1$H NMR δ 1.95 (s, 3H), δ 2.29 (dd, 1H), δ 2.53 (dd, 1H), δ 3.16 (p, 1H), δ 4.17 (dd, 1H), δ 4.25 (dd, 1H), δ 5.60 (t, 1H), δ 6.15 (s, 1H). RI (E-line) was 1.509; and Abbe was 38.

Part 3

Preparation of Examples 1-11

Example 1

Prepolymerization of TGMA (50%) and Styrene (50%)

A 1-L round-bottom flask fitted with a condenser and a magnetic stir bar was charged with TGMA made according to the procedure of CE-1 (50 g, 0.32 mol) and styrene (50 g, 0.48 mol) under a nitrogen atmosphere. Vazo 67 (2,2'-azobis (2-methylbutyronitrile) (0.05 g, 0.26 mmol) was added and then the reaction mixture was heated to between 105-110° C. in an oil bath. While heating, the viscosity of the reaction mixture at 25° C. was monitored every 15 minutes. After 1 hour at the above temperature the reaction reached a stable viscosity at which point the reaction mixture was removed from the heat. It was allowed to cool to room temperature while being exposed to air (in order to activate the MEHQ radical inhibitor introduced through the TGMA). Upon cooling, the reaction product was homogeneous, clear, colorless oil (100 g) with a viscosity of 325 cP at 25° C. The product was stored at 4° C. FT-Raman spectrum showed that 40% of the total polymerizable double bonds were converted to polymer during the reaction. Of each monomer, 48% of the TGMA and 35% of the styrene were converted to polymers. RI (E-line) was 1.5487 and Abbe was 29.5.

Example 2

Prepolymerization of TGMA (60%) and Styrene (40%)

The procedure of Example 1 was followed except that the following in the amounts indicated were used: TGMA (300 g, 1.89 mol), styrene (200 g, 1.92 mol), and Vazo 67, reported to be 2,2'-azobis(2-methylbutyronitrile), (0.25 g, 1.3 mmol). Upon cooling the reaction product was homogeneous, clear, colorless oil (500 g) with a viscosity 210 cP at 25° C. The product was stored at 4° C. FT-Raman spectrum showed that 28.5% of the total polymerizable double bonds were converted to polymer during the reaction. Of each monomer, 29% of the TGMA and 28% of the styrene were converted to polymers. RI (E-line) 1.5434 and Abbe 30.9 were measured.

Example 3

Preparation of Michael Adduct of DMDS and TGMA in a One Pot Process

A 5-L jacketed reactor was fitted with a mechanical stirrer, a thermometer, and a condenser. The reactor was charged with GMA (300 g, 2.11 mol) and DABCO, reported to be diazabicyclooctane, (240 mg, $2.1 \times 10^{-3}$ mol) under a nitrogen atmosphere. The resulting mixture was then cooled to 0° C. and DMDS, (160 g, 1.04 mol) was added slowly to ensure no increase in temperature (1-mL per minute). After the DMDS was added, the reaction was stirred at 0° C. for two hours, and a titration with iodine showed no free thiol to be present. The reaction was treated with acetic anhydride (23 g, 0.23 mol) and allowed to warm to room temperature at which point the mixture was diluted with toluene (1 L) and methanol (1 L). The mixture was then heated to 40° C., and thiourea (180 g, 2.37 mol) was added in ≈50 g portions in 15 minute intervals. During these additions, the temperature of the reaction was monitored to maintain a temperature range of 40° C.-50° C. After the final portion was added, the reaction was stirred at this temperature for three hours after which TLC analysis (20% ethylacetate in hexanes) showed no remaining Michael adduct of DMDS with GMA. The reaction mixture was poured into a 4-L separatory funnel. The reaction mixture was washed twice with 800-mL portions of dilute $H_2SO_4$ (1 weight % in water). The mixture was then washed twice with 800-mL portions of saturated aqueous sodium chloride solution. The organic layer was separated, recovered and dried over magnesium sulfate and concentrated under vacuum. Clear oil was obtained upon filtration through a 0.45 μm filter press (375 g). Purity of the obtained product was determined by NMR analysis to be 94% DMDS-TGMA Michael Adduct and 6% TGMA. The viscosity of the product was 237 cP at 25° C. $^1$H NMR: d 1.18 (d, 6H), d 2.19 (dd, 2H), d 2.45 (dd, 2H), d 2.56 (dd, 2H), d 2.64 (m, 2H), d 2.66 (s, 8H), d 2.77 (dd, 2H), d 3.05 (p, 2H), d 4.09 (dd, 4H). RI (E-line) was 1.5628 and Abbe was 40.5.

Example 4

Preparation of Michael Adduct of DMDS and TGMA in a One Pot Process

The procedure of Example 3 was followed except that the following materials in the amounts indicated were used: GMA (420 g, 2.96 mol), DABCO (24 mg, $2.2 \times 10^{-4}$ mol), DMDS, (33.5 g, 0.22 mol), acetic anhydride (33 g, 0.32 mol), toluene (1 L), methanol (1 L), and thiourea (250 g, 3.29 mol). The recovered organic layer was stabilized with MEHQ (50 mg, 0.4 mmol), dried over magnesium sulfate, and concentrated under vacuum. Clear oil was obtained upon concentration (417 g). NMR spectra were consistent with a mixture of the two components, thioglycidyl methacrylate and DMDS-TGMA Michael adduct (NMR spectra reported in CE-1 and Example 3) in a 10:1 molar ratio. RI (E-line) was 1.5288 and Abbe was 39.5.

Example 5

Preparation of Michael Adduct of GST and TGMA in a One Pot Process

The procedure of Example 3 was followed except that the following materials in the amounts indicated were used: GMA (300 g, 2.11 mol), DABCO (240 mg, $2.1 \times 10^{-3}$ mol), GST (180 g, 0.69 mol), acetic anhydride (23 g, 0.23 mol), toluene (1 L), methanol (1 L), and thiourea (180 g, 2.37 mol). Slightly hazy oil was obtained upon concentration (380 g). The viscosity of this product was 615 cP at 25° C. $^1$H NMR: d 1.27 (d, 9H), d 2.29 (d, 3H), d 2.54 (d, 3H), d 2.67 (dd, 3H), d 2.71 (m, 3H), d 2.76 (s, 8H), d 2.88 (m, 3H), d 2.91 (m, 4H), d 3.00 (p, 1H), d 3.15 (p, 3H), d 4.19 (dd, 6H). RI (E-line) was 1.5677 and Abbe was 39.7.

Example 6

Preparation of Michael Adduct of GST and TGMA in a One Pot Process

The procedure of Example 3 was followed except that the following materials in the amounts indicated were used: GMA (420 g, 2.95 mol), DABCO (45 mg, $4 \times 10^{-4}$ mol), GST (35 g, 0.13 mol), toluene (1 L), methanol (1 L) and thiourea (250 g, 3.29 mol). The organic layer was stabilized with MEHQ (50 mg, 0.4 mmol), dried over magnesium sulfate, and concentrated under vacuum. Clear oil was obtained upon concentration (412 g). NMR spectra of the sample are consistent with a mixture of TGMA and GST-TGMA Michael adduct (NMR spectra reported in CE-1 and Example 5) in a ratio of 94:6. The viscosity of this product was lower than 50 cP at 25° C. RI (E-line) was 1.5177 and Abbe was 38.9.

Example 7

Prepolymerization of a Mixture Containing TGMA, Example 5 and Styrene

A 500-mL round-bottom flask fitted with a condenser and a magnetic stir bar was charged material made according to the procedure of CE-1 (96 g), material made according to the procedure of Example 5 (24 g) and styrene (80 g) under a nitrogen atmosphere. Vazo 67 (0.10 g) was added and the reaction mixture was heated to between 105-110° C. in an oil bath. While heating, the viscosity of the reaction mixture at 25° C. was monitored every 15 minutes. After 1 hour at the above temperature range the reaction reached a stable viscosity at which point the reaction mixture was removed from the heat. It was allowed to cool to room temperature while being exposed to air (in order to activate the MEHQ radical inhibitor in the TGMA). Upon cooling the reaction product was homogeneous, clear, colorless oil (200 g). The viscosity of the product was 75 cP at 25° C. RI (E-line) was 1.5477 and Abbe was 30.8. The resulting product was stored at 4° C.

Example 8

Prepolymerization of the Material Described in Example 6 (60%) and Styrene (40%)

A 500-mL round-bottom flask fitted with a condenser and a magnetic stir bar was charged with material made according to the procedure of Example 6 (120 g) and styrene (80 g) under a nitrogen atmosphere. Vazo 67 (0.10 g) was added and the reaction mixture was heated to between 105-110° C. in an oil bath. While heating, the viscosity of the reaction mixture at 25° C. was monitored every 15 minutes. After 1 hour at the above temperature range the reaction reached a stable viscosity at which point the reaction mixture was removed from the heat and MEHQ (70 mg) was added. It was allowed to cool down to room temperature while being exposed to air in order to activate the MEHQ radical inhibitor. Upon cooling the reaction product was homogeneous, clear, colorless oil (200 g). The viscosity of the product was 100 cP at 25° C. RI (E-line) was 1.5504 and Abbe was 30.9. The resulting product was stored at 4° C.

Example 9

Prepolymerization of the Material Described in Example 4 (60%) and Styrene (40%)

The procedure of Example 8 was followed except that the following materials in the amounts indicated were used: material made according to the procedure of Example 4 (180 g), styrene (120 g), Vazo 67 (0.225 g), and MEHQ (70 mg). Upon cooling the reaction product was homogeneous, clear, colorless oil (300 g, 100% yield). The viscosity of the product was 1195 cP at 25° C. RI (E-line) was 1.5513 and Abbe was 30.8. The resulting product was stored at 4° C.

Example 10

Prepolymerization of TGMA (70%), MMA (20%) and PTMA (10%)

A 100 mL round-bottom flask fitted with a condenser and a magnetic stir bar was charged with TGMA made according to the procedure of CE-1 (28 g), MMA (8 g) and PTMA (4 g) under a nitrogen atmosphere. LUPEROX® 256 peroxide (0.4 g) was added and the reaction mixture was heated to 70° C. in an oil bath. While heating, the viscosity of the reaction mixture at 25° C. was monitored every 15 minutes. After 2 hours at the above temperature the reaction reached a stable viscosity at which point the reaction mixture was removed from the heat. It was allowed to cool down to room temperature while being exposed to air (in order to activate the MEHQ radical inhibitor introduced through the TGMA). Upon cooling the reaction product was homogeneous, clear, colorless oil (40 g) with viscosity 595 cP at 25° C. The resulting product was stored at 4° C. RI (E-line) was 1.5200 and Abbe was 43.3.

Example 11

Preparation of Prepolymer Containing TGMA (54%), Styrene (36%) and BPA-TDGE (10%)

A 100 mL round-bottom flask fitted with a condenser and a magnetic stir bar was charged with TGMA made according to the procedure of CE-1 (21.6 g), styrene (14.4 g) and BPA-TDGE (4.0 g) under a nitrogen atmosphere. LUPEROX® 256 peroxide (0.04 g) was added and the reaction mixture was heated to 95° C. in an oil bath. While heating, the viscosity of the reaction mixture at 25° C. was monitored every 15 minutes. After 1 hour at the above temperature the reaction reached a stable viscosity at which point the reaction mixture was removed from the heat. It was allowed to cool to room temperature while being exposed to air in order to activate the MEHQ radical inhibitor introduced through the TGMA. Upon cooling, the reaction product was homogeneous, clear, colorless oil (40 g) with viscosity 150 cP at 25° C. The product was stored at 4° C. RI (E-line) was 1.5520 and Abbe was 31.5. The BPA-TDGE used in this experiment was synthesized by reacting Bisphenol A diglycidyl ether with thiourea in the same process used to prepare CE-1.

Part 4

Procedure Used for Casting a Polymer Sample of Examples 1, 2, 8-11 and CE-1

The casting formulations (CF) listed in Tables 1 and 2 were added to a glass jar and mixed until homogeneous. The radical initiator and base catalyst were added to this mixture and stirred until fully dissolved. The resulting material was filtered through a 0.45 micron filter and degassed under vacuum for 10 min and poured into a glass mold. The cast material was cured for 26 hours at gradually increasing temperature from 70° C. to 95° C. (Cure Cycles 1 and 3) or for 25 hours at gradually increasing temperature from 50° C. to 120° C. (Cure Cycle 2). The sample was demolded and postcured for 3 hours at 120° C. The curing cycles are listed in Table 3 and the properties of the cast polymers are included in Table 4 and 5.

TABLE 1

Casting Formulations CF-1 to CF-7 of Examples 1 and 2

| Example # & Monomer Composition (% Weight) | CF-1 | CF-2 | CF-3 | CF-4 | CF-5 | CF-6 | CF-7 |
|---|---|---|---|---|---|---|---|
| Example 1 | 88 | | | | | | |
| Example 2 | | 96 | 100 | 88 | 86 | 88 | 97 |
| DVB | 10 | | | 10 | 10 | 10 | |
| DMDS | | 4 | | 2 | 4 | | |
| GST | 2 | | | | | 2 | 3 |
| Catalysts | | | | | | | |
| TBPB | 1.00 | 0.72 | 0.72 | 1.00 | 0.80 | 1.00 | 1.00 |
| LUPEROX® 256 | 1.00 | 1.00 | 1.30 | 1.00 | 1.00 | 1.00 | 1.00 |
| Cure Cycle | | | | | | | |
| 1 | X | | | | | X | X | X |
| 2 | | | | X | | | |
| 3 | | X | X | | | | |

TABLE 2

Casting Formulations CF-8 to CF-14 of Comparative Example 1 (CE-1) and Examples 8-11

| Example # & Monomer Composition (% Weight) | CF-8 | CF-9 | CF-10 | CF-11 | CF-12 | CF-13 | CF-14 |
|---|---|---|---|---|---|---|---|
| CE-1 | 96 | 75 | | | | | |
| Example 8 | | | 90 | | | | |
| Example 9 | | | | 90 | 89 | | |
| Example 10 | | | | | | 100 | |
| Example 11 | | | | | | | 90 |
| BPA-TDGE | | | | | | | 10 |
| DVB | 4 | | 10 | 10 | 10 | | 10 |
| DMDS | | | | | | | |
| GST | | 25 | | | | 2 | 3 |

TABLE 2-continued

Casting Formulations CF-8 to CF-14 of Comparative Example 1 (CE-1) and Examples 8-11

| Example # & Monomer Composition (% Weight) | CF-8 | CF-9 | CF-10 | CF-11 | CF-12 | CF-13 | CF-14 |
|---|---|---|---|---|---|---|---|
| Catalysts | | | | | | | |
| TBPB | 0.72 | | 1.00 | 1.00 | 1.00 | 0.72 | 0.72 |
| DABCO | | 0.40 | | | | | |
| LUPEROX ® 256 | 1.00 | 1.40 | 1.00 | 1.00 | 1.00 | 1.00 | 0.43 |
| Curing Cycle | | | | | | | |
| 1 | | | | | X | | |
| 2 | | | X | X | | | |
| 3 | X | X | | | | X | X |

TABLE 3

Cure Cycles 1, 2 and 3

| | Cure Cycle 1 | | Cure Cycle 2 | | Cure Cycle 3 | |
|---|---|---|---|---|---|---|
| Step # | Time (hours) | Temperature (° C.) | Time (hours) | Temperature (° C.) | Time (hours) | Temperature (° C.) |
| 1 | 0.5 | 71-74 | 24 | 50-120 | 0.5 | 71-74 |
| 2 | 6.5 | 74 | 1 | 120 | 3.5 | 74 |
| 3 | 0.5 | 74-77 | | | 0.5 | 74-77 |
| 4 | 6.5 | 77 | | | 3.5 | 77 |
| 5 | 0.33 | 77-79 | | | 0.33 | 77-79 |
| 6 | 2.5 | 79 | | | 2.5 | 79 |
| 7 | 0.5 | 79-82 | | | 0.5 | 79-82 |
| 8 | 2.5 | 82 | | | 1.5 | 82 |
| 9 | 1 | 82-88 | | | 1 | 82-88 |
| 10 | 2 | 88 | | | 1 | 88 |
| 11 | 1.17 | 88-95 | | | 1.17 | 88-95 |
| 12 | 2 | 95 | | | 1 | 95 |

TABLE 4

Properties of Polymers made with Examples 1 (CF-1) and 2 (CF2-7)

| Properties | CF-1 | CF-2 | CF-3 | CF-4 | CF-5 | CF-6 | CF-7 |
|---|---|---|---|---|---|---|---|
| FMH | 146 | 126 | 144 | 130 | 131 | 145 | 135 |
| RI | 1.588 | 1.591 | 1.484 | 1.590 | 1.593 | 1.589 | 1.589 |
| Abbe | 35 | 36 | 37 | 35 | 36 | 37 | 37 |
| Thermal Properties | Good* | Good* | Good* | Good* | Good* | Good* | Good* |
| Appearance | Clear | Clear | Clear | Clear | Clear | Clear | Clear |
| YI | 4.00 | 3.68 | 3.42 | 3.70 | 3.10 | 3.10 | 3.60 |

*Thermal properties are good when the Tg of the polymerizate is >80° C. (DMA).

TABLE 5

Properties of Polymers made with CE-1 (CF-8 & 9) and Examples 8-11 (CF-10-14)

| Properties | CF-8 | CF-9 | CF-10 | CF-11 | CF-12 | CF-13 | CF-14 |
|---|---|---|---|---|---|---|---|
| FMH | 125 | 72 | 136 | 151 | 145 | 103 | 148 |
| RI | 1.590 | 1.382 | 1.590 | 1.591 | 1.591 | 1.562 | 1.590 |
| Abbe | 37 | 38 | 36 | 36 | 36 | 45 | 36 |
| Thermal Properties | Bad** | Bad** | Good* | Good* | Good* | Good* | Good* |
| Appearance | Clear | Hazy | Clear | Clear | Clear | Clear | Clear |
| YI | 3.25 | 10.74 | 5.80 | 4.10 | 3.42 | 6.67 | 4.39 |

**Thermal properties are bad when the Tg of the polymerizate is <80° C. (DMA). Such materials are not acceptable for optical material and cannot be processed as a lens.

The present invention has been described with reference to specific details of particular embodiments thereof. It is not intended that such details be regarded as limitations upon the scope of the invention except insofar as and to the extent that they are included in the accompanying claims.

What is claimed is:

1. A thioepoxide functional, polymerizable composition comprising a reaction product of:
    (a) thiourea; and
    (b) an epoxide functional, polymerizable composition comprising a reaction product prepared from a reaction mixture comprising:
        (i) a monomer comprising at least one ethylenically unsaturated ester functional monomer having an epoxide functional group; and
        (ii) a compound having two or more thiol groups, wherein the reactants (i) and (ii) are reacted via a Michael addition reaction in the presence of a base to form an epoxide functional reaction product.

2. A polymerizable composition comprising a reaction product of:
    (a) a monomer composition comprising at least one ethylenically unsaturated ester functional monomer having a thioepoxide functional group; and
    (b) a thioepoxide functional, polymerizable composition comprising a reaction product of:
        (1) thiourea; and
        (2) an epoxide functional, polymerizable composition comprising a reaction product prepared from a reaction mixture comprising:
            (i) a monomer comprising at least one ethylenically unsaturated ester functional monomer having an epoxide functional group; and
            (ii) a compound having two or more thiol groups, wherein the reactants (i) and (ii) are reacted via a Michael addition reaction in the presence of a base to form an epoxide functional reaction product.

3. The polymerizable composition of claim 2, wherein the monomer composition (a) further comprises at least one different polymerizable ethylenically unsaturated monomer.

4. The polymerizable composition of claim 3, wherein the different polymerizable ethylenically unsaturated monomer comprises at least one of styrene, divinyl benzene, an alkyl acrylate, and an alkyl methacrylate.

5. An optical article comprising a polymer prepared from the polymerizable composition of claim 4.

* * * * *